(12) United States Patent
Cima et al.

(10) Patent No.: US 9,395,286 B2
(45) Date of Patent: Jul. 19, 2016

(54) DEVICE AND METHOD FOR SAMPLING BODILY FLUID FOR MEDICAL ANALYTES IN ULTRA LOW CONCENTRATIONS

(75) Inventors: Michael J. Cima, Winchester, MA (US); Gregory J. Ekchian, Belmont, MA (US); Christophoros C. Vassiliou, Cambridge, MA (US); Vincent H. Liu, Cambridge, MA (US); Christoph Wald, Nahant, MA (US); Sebastian Flacke, Nahant, MA (US); Fredric D. Gordon, Newton, MA (US)

(73) Assignees: Massachusetts Institute of Technology, Cambridge, MA (US); Lahey Clinic Foundation, Inc., Burlington, MA (US)

( * ) Notice: Subject to any disclaimer, the term of this patent is extended or adjusted under 35 U.S.C. 154(b) by 0 days.

(21) Appl. No.: 13/977,108

(22) PCT Filed: Dec. 30, 2011

(86) PCT No.: PCT/US2011/068165
§ 371 (c)(1),
(2), (4) Date: Sep. 5, 2013

(87) PCT Pub. No.: WO2012/094251
PCT Pub. Date: Jul. 12, 2012

(65) Prior Publication Data
US 2014/0004503 A1    Jan. 2, 2014

Related U.S. Application Data

(60) Provisional application No. 61/429,658, filed on Jan. 4, 2011.

(51) Int. Cl.
| | | |
|---|---|---|
| *C12M 1/34* | (2006.01) | |
| *C12M 1/00* | (2006.01) | |
| *C12Q 1/70* | (2006.01) | |
| *G01N 33/53* | (2006.01) | |

(Continued)

(52) U.S. Cl.
CPC .. *G01N 1/34* (2013.01); *A61F 2/01* (2013.01); *G01N 33/5302* (2013.01); *G01N 33/5306* (2013.01); *G01N 33/54313* (2013.01)

(58) Field of Classification Search
None
See application file for complete search history.

(56) References Cited

U.S. PATENT DOCUMENTS

| 5,893,869 A | 4/1999 | Barnhart et al. |
| 6,444,461 B1 | 9/2002 | Knapp et al. |

(Continued)

FOREIGN PATENT DOCUMENTS

WO    2006133392 A1    12/2006

OTHER PUBLICATIONS

McDonald et al., "Poly(dimethylsiloxane) as Material for Fabricating Microfluidic Devices," Accounts of Chemical Research, vol. 35, No. 7: 491-499 (2002).*

(Continued)

*Primary Examiner* — Benjamin P Blumel
*Assistant Examiner* — M. Franco Salvoza
(74) *Attorney, Agent, or Firm* — Sutherland Asbill & Brennan LLP

(57) ABSTRACT

Trapping devices and methods are provided for capturing a medical analyte, in blood or another biological fluid. The device may include a structural substrate and a binding agent, such as an antibody, affixed to the structural substrate, wherein the binding agent is capable of binding or attaching with a medical analyte, such as a viral particle, and the device is configured for placement in a biological cavity or vessel (containing a biological fluid) in a patient. The trapping device, which may be in a twisted coil shape, is configured to trap at least some of the medical analyte, such a viral particle, present in the biological fluid. The method may include deploying a trapping device into the patient's blood vessel; after a period following the deployment, removing the trapping device from the biological cavity or blood vessel; and then analyzing the trapping device for the presence of the medical analyte.

12 Claims, 3 Drawing Sheets

(51) Int. Cl.
  *G01N 1/34* (2006.01)
  *A61F 2/01* (2006.01)
  *G01N 33/543* (2006.01)

(56) References Cited

U.S. PATENT DOCUMENTS

| | | | |
|---|---|---|---|
| 6,482,222 B1 | 11/2002 | Bruckheimer et al. | |
| 6,538,114 B1* | 3/2003 | Persson et al. | 530/388.3 |
| 2003/0093111 A1* | 5/2003 | Ken | A61B 17/12022 606/200 |
| 2005/0004598 A1* | 1/2005 | White | A61B 17/12022 606/200 |
| 2006/0099236 A1* | 5/2006 | Gutterman | 424/422 |
| 2007/0055365 A1* | 3/2007 | Greenberg et al. | 623/1.44 |
| 2007/0141099 A1* | 6/2007 | Buiser | A61B 17/12022 424/422 |
| 2008/0176271 A1* | 7/2008 | Silver et al. | 435/29 |
| 2008/0241847 A1 | 10/2008 | Hoon et al. | |
| 2009/0270908 A1* | 10/2009 | Tekulve | A61B 17/12022 606/200 |

OTHER PUBLICATIONS

Shin, Joong, et al., "Non-Invasive Testing for Rupture of the Fetal Membranes", US Obstetrics and Gynecology, vol. 1, Jan. 1, 2007, pp. 13-16, XP55024018.

Ekchian, Gregory J., "Design and Evaluation of a Device for Trapping Hepatitis C Viral Particles at Ultra Low Concentrations", Jan. 4, 2011, pp. 1-58, XP055023816, Boston, retrieved from the internet: URL:http://dspace.mit.edu/bitstream/handle/1721.1/62675/714257917.pdf?sequence=1 [retrieved on Apr. 4, 2012].

Du, Z., N. Coils, K.H. Cheng, M.W. Vaughn, and L. Gollahon, "Microfluid-based Diagnostics for Cervical Cancer Cells", Biosensors and Bioelectronics 21 (2006): 1991-1995. Science Direct. Web. Mar. 2010.

Schrama, et al., "Antibody Targeted Drugs as Cancer Therapeutics", Nature Reviews, Drug Discovery, vol. 5, pp. 147-159 (Feb. 2006).

Perez, Manuel, J., et al. "Viral-Induced Self-Assembly of Magnetic Nanoparticles Allows the Detection of Viral Particles in Biological Media", J. Am. Chem. Soc., 2003, 125 (34), pp. 10192-10193.

* cited by examiner

DEVICE AND METHOD FOR SAMPLING BODILY FLUID FOR MEDICAL ANALYTES IN ULTRA LOW CONCENTRATIONS

CROSS-REFERENCE TO RELATED APPLICATIONS

This application is a national phase entry of PCT Patent Application No. PCT/US2011/068165, filed on Dec. 30, 2011, designating the United States of America, and claims priority to U.S. Provisional Application No. 61/429,658, filed on Jan. 4, 2011, which is incorporated by reference herein in its entirety.

BACKGROUND

Proper treatment of diseases or medical conditions such as hepatitis C (HCV) frequently requires close monitoring of the amount of foreign materials, such as viral particles or pathogens, present in bodily fluids. The HCV virus present in the patient's blood, for example, is clinically referred to as the viral load and needs to be determined. Currently a blood sample is taken from the patient and viral particles are quantified, usually using PCR (Polymerase Chain Reaction) or TMA (Transcription Mediated Amplification) technology known in the art. Initial quantification of a patient's viral load can typically be obtained using commercially available tests because such patients typically have a sufficiently high viral load, one well within the detectable range of the most commonly used tests. Exemplary HCV detection tests may have a quantification range of approximately 108 viral particles to 172,000,000 viral particles per mL. Although more sensitive tests are available, these high sensitivity tests may have a small dynamic range and may be used in the limited cases when a physician knows a patient has a low viral load.

The number of particles that can be captured from a patient during testing is typically limited by the amount of bodily fluid that can be sampled. For example, physicians may sample between 1 mL and 3 mL of blood for each HCV test conducted. If the patient has a low level of viral particles in his or her blood, so low that a 3 mL blood draw may not contain any viral particles or a number insufficient for detection using PCR or TMA, then the test result will be undetectable (negative). These negative results can in many cases be classified as a false negative, because the patient is still infected but the viral level is too low to detect. Past improvements of HCV diagnostics have focused on enhancing the amplification methods in order to be able to detect lower concentrations of a virus in a traditional blood draw. While this has provided significant improvements for detecting the viral particles that are present in the sample, these traditional methods may still be ineffective, such as when the blood sample contains no viral particles.

Many HCV patients undergoing treatment will reach a point where current methods, even the most sensitive tests, may be insufficient to determine the true viral load. Some patients may achieve this undetectable level in only 4 weeks, or earlier, into a typical 48 week treatment. If a physician stops treatment in response to an undetectable result and a patient is still infected, then a patient may have a higher likelihood of relapsing than if treatment had been continued for the full term. Accordingly, physicians typically are forced to continue treatment for the clinically recommended length to avoid increasing the chance of relapse even if a patient may actually be cured. Furthermore, if the patient relapses, the viral infection may be harder to treat because the virus may be resistant to medication since it has already been exposed to treatment.

It would therefore be desirable to provide means and methods for accurately detecting and quantifying low viral loads or other materials that may affect patient health. It would also be desirable to provide an accurate quantification of such materials in order to determine whether the length of the patient's treatment may be shortened, thereby reducing the significant side-effects and costs associated with extended treatment.

SUMMARY

Trapping devices and methods are provided for capturing a medical analyte, particularly in blood or other fluid in vivo. In one aspect, a trapping device is provided that includes a structural substrate and at least one binding agent, such as an antibody, affixed to the structural substrate, wherein the binding agent is capable of binding or attaching with a medical analyte, such as a viral particle, and the trapping device is dimensioned and adapted for placement in a biological cavity or vessel in a patient, which cavity or vessel contains a biological fluid. The trapping device, which may be in the shape of a twisted coil, is configured to trap at least a portion of the medical analyte present in the biological fluid.

In a particular embodiment, a viral particle trapping device is provided for sampling a viral particle. In one embodiment, the viral particle device includes a structural substrate; and a plurality of antibodies capable of binding with the viral particle affixed to the structural substrate, wherein the trapping device is dimensioned and adapted for placement in a biological cavity or vessel in a patient, which cavity or vessel contains a biological fluid, the trapping device being configured to trap at least a portion of the medical analyte present in the biological fluid. The structural substrate may comprise a NITINOL wire in a twisted coil configuration providing a tortuous fluid flow path around and through the twisted coil configuration.

In another aspect, a method is provided for analyzing for the presence of a medical analyte in a patient. In one embodiment, the method includes deploying a trapping device into a biological cavity or blood vessel (such as the hepatic vein or superior vena cava) of a patient; after a period of time following the deployment, removing the trapping device from the biological cavity or blood vessel; and then analyzing the trapping device for the presence of the medical analyte. In one embodiment, the step of analyzing the trapping device includes placing the trapping device in a fluid; transferring the medical analyte, if any, or a component of the medical analyte, if any, from the trapping device to the fluid; and analyzing the fluid for the presence of the medical analyte or the component of the medical analyte, for example by using a PCR or TMA based test, ELISA, fluorescence or mass spectroscopy. In another embodiment, the trapping device may be inserted into an extracorporeal device in which bodily fluid may flow for a period of time.

In another aspect, a method is provided for selectively obtaining and analyzing a constituent of a patient's bodily fluid, the method comprising: providing a device for collecting the constituent from the bodily fluid, the device comprising a material that has an affinity to the constituent; deploying the device into a location to contact the bodily fluid for a predetermined period, wherein a quantity of the constituent adheres to the material; and thereafter; removing the device from the location. In one embodiment, the method further includes after removing the device, analyzing the device to determine the quantity or presence of the constituent, if any, that has adhered to the device.

DETAILED DESCRIPTION

Figure 1A:
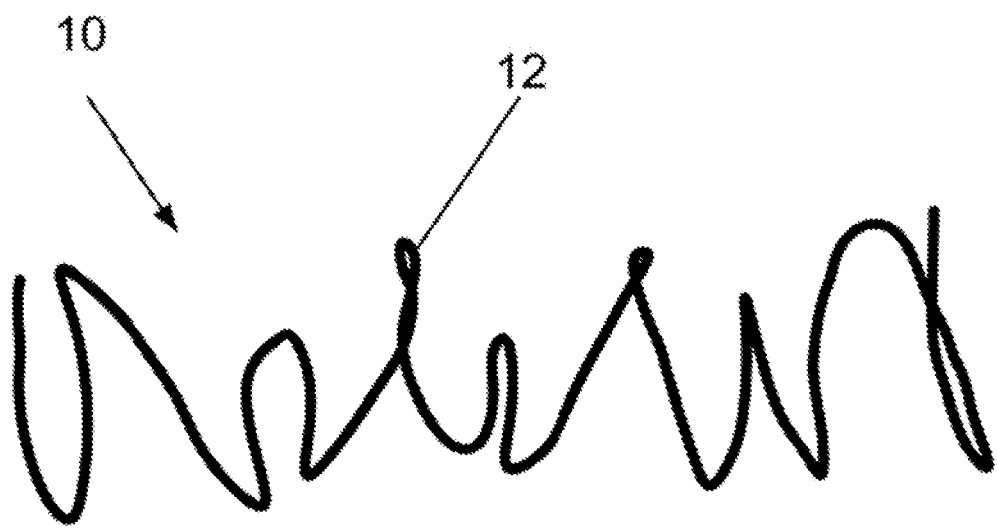
FIG. 1A is a side view, illustrating a twisted coil viral particle trapping device according to one or more embodiments of the present invention.

Viral particle trapping devices have been developed that may be used in conjunction with currently-available diagnostic tests to overcome deficiencies of conventional sampling methods. These devices preferentially capture and retain viral particles from fluids, such as blood, so that a detectable sample can be analyzed. The viral particle trapping device is designed to be temporarily deployed into a biological cavity or blood vessel, such as in a vein of the patient, via a catheter. The device may be oriented so that blood passes over and/or around the device as the blood travels through the vein. In one embodiment of the device, it is coated with antibodies that are specific to a viral particle such as hepatitis C, so that when the viral particle comes in contact with the device, the viral particle binds to the antibodies and is trapped. The device is then removed and the number of trapped viral particles quantified using various tests, including currently available tests, such as PCR-based tests, TMA-based tests or other forms of detection such as ELISA (enzyme-linked immunosorbent assay). The device may be withdrawn after it has remained deployed for a relatively short period of time, e.g., from 10 minutes to 30 minutes. The number of viral particles trapped by the device may be converted to a concentration or viral load based on the actual or estimated volume of blood sampled. Physicians can then determine the best course of treatment with this much more sensitive measurement. This in-vivo blood sampling technique advantageously may allow approximately 40,000 times more blood to be sampled in a 30-minute period than with a traditional blood draw (approximately 2 mL). In an alternative embodiment, the trapping device may be inserted into an extracorporeal line or device in which bodily fluid is flowing.

Although the present disclosure is described primarily in context of HCV sampling and analysis, it should be noted that the trapping device may be used to trap other medical analytes or foreign substances, such as small molecules, circulating DNA, pathogens or cells, for example, by employing binding agents (e.g. antibodies, aptamers or polymers) that are appropriate for binding to a particular substance. Medical analytes that may be captured include, for example, hepatitis A viral particles, hepatitis B viral particles, HIV (human immunodeficiency virus) viral particles, HPV (human papillomavirus) viral particles or circulating cancer cells.

An antibody is a protein that is naturally created by the body's immune system when it detects a foreign body (e.g., HCV particles). The viral particles, which may also be referred to as antigens, will bind to the antibodies when they come in contact with each other. While antibodies are produced by the body naturally, they can also be created ex vivo, such as in another animal species. In some embodiments, HCV antibodies may be added to the device to trap HCV particles. The HCV antibodies may be specific to the proteins (E1 and E2) expressed on the surface of the HCV particle. These surface proteins may also be referred to as surface antigens. Other types of antibodies may be provided on the device to trap the other corresponding types of viral particles. Many other types of targeting ligands may be considered. Indeed, and type of ligand with an affinity to the desired analytes can be considered. For example, complementary DNA can be used to target specific strands of DNA circulating in the body fluid.

Viral Particle Trapping Devices

Viral particle trapping devices are provided for analyzing the presence and/or concentration of one or more particular viral particles in a bodily fluid, such as blood, in vivo. Advantageously, the viral particle trapping devices may be deployed in a biological cavity or blood vessel, such as in a vein, subarachnoid cavity or bladder, and may be used to trap viral particles that contact the device for subsequent measurement procedures.

In an alternative embodiment, the trapping device may be incorporated or inserted into an extracorporeal device in which blood or another bodily fluid may flow for a period of time. Examples of such extracorporeal devices include extracorporeal circulation equipment known in the art, including for example, in hemodialysis, hemofiltration, extracorporeal membrane oxygenation, and cardiopulmonary bypass.

Figure 1B:
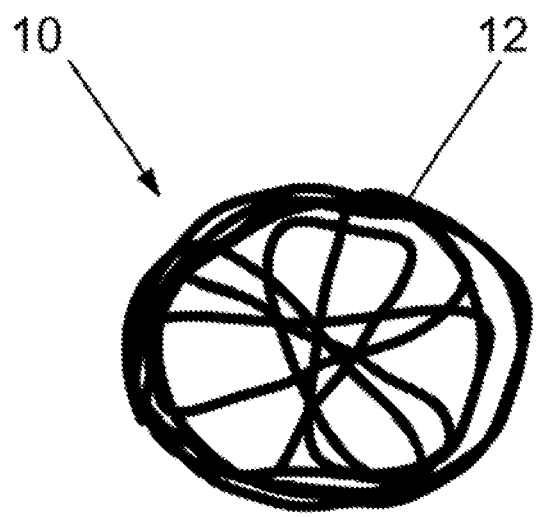
FIG. 1B is an end view as would be seen looking into a blood vessel, illustrating the twisted coil viral particle trapping device of FIG. 1A.

In some embodiments, the viral particle trapping device is in the shape of a twisted coil. The term "twisted coil" as used herein describes a shape that may be formed by forming a shape that is substantially not straight, such as a helix of one or more loops. The shape may be formed by other methods other than altering a helix however. An exemplary embodiment of a twisted coil is illustrated in FIG. 1A and FIG. 1B. Such shapes may be configured to maximize the interaction of the device with the fluids, such as by maximizing the intersection of viral trapping surfaces with a fluid flow field. As illustrated in FIGS. 1A and 1B, the viral particle trapping device 10 may include a twisted coil structure 12 that, when deployed, crosses back and forth across the lumen of a blood vessel, perpendicular to the direction of the blood flow (in contrast with merely circling the inner surface of the blood vessel). This allows the device to take advantage of the flowing blood to carry the viral particles to the surface of the device. For example, looking within the blood vessel in the direction of blood flow, one may see the viral particle trapping device as illustrated in FIG. 1B. Although it may appear from this view as if a large amount of the blood vessel is blocked, this is not the case as can be seen in FIG. 1A. Looking at the device from the side, each time one of the "loops" of the structure 12 crosses the blood vessel it may be a distance downstream of the previous location where one of the loops crosses the blood vessel. The separation distance between the loops may be, for example, about 0.3 cm to about 1.0 cm, or about, 0.5 cm. Accordingly, in some embodiments, the twisted coil structure 12 may not block more than a small percentage of the cross-sectional area blood vessel perpendicular to the flow at any location of the blood vessel. For example, the structure may occlude less than 8%, or less than 4%, of the blood vessel in the cross-section perpendicular to the flow of blood at any location within the blood vessel. Thus in one embodiment, the structural substrate may comprise a NITINOL wire in a twisted coil configuration providing a tortuous fluid flow path around and through the twisted coil configuration.

In some embodiments, the device 10 may sample over 85,000 mL of blood in a 30 minute period, such as when deployed in a particular blood vessel, e.g., the superior vena cava (SVC). Thus, in some embodiments the device 10 may allow a volume of blood to be sampled that is more than 40,000 times greater than the volume sampled in current blood draw techniques. When placed in the hepatic veins, the device may sample 10,000 times more blood than a traditional blood draw. The device may be deployed in other intravascular sites depending, for example, on the sizes of the blood vessel and the device and the blood volume contact desired for the particular viral diagnostic test being used.

While the volume of blood sampled is one important factor, the ability of the viral particles to be captured and retained by the antibodies is also important. Researchers have examined the binding efficiency of viral particles to antibodies in flowing blood. See Du, Z., N. Colts, K. H. Cheng, M. W. Vaughn, and L. Gollahon. "Microfludic-based Diagnostics for Cervical Cancer Cells." *Biosensors and Bioelectronics* 21 (2006): 1991-1995. *Science Direct. Web.* 10 Mar. 2010. Specifically, the binding efficiency of antibodies for HPV (Human Papaloma Virus) viral particles was studied at a blood flow rate of 0.13 cm/s. For example, the binding efficiency of the HPV antibodies at this velocity was determined to be in excess of 30%. This is slower than the rate of blood flow in the SVC (average 22.5 cm/s), but researchers also found that the trapping efficiency plateaued at 30% as blood velocity increased.

Tables 1 and 2 below illustrate estimated values for the number of hepatitis C viral particles that may be captured for various binding efficiencies and viral particle concentrations during a 30 minute period. Table 1 shows the number of such viral particles that would be trapped by the device for three different viral particle concentrations and five different binding efficiencies if the device was placed in the SVC. Table 2 shows the number of such viral particles that could be trapped by the device for three different viral particle concentrations and five different binding efficiencies if the device was placed in the hepatic veins. The number of viral particles captured is preferably greater than 30 (the minimum quantifiable amount with the Abbott quantifiable PCR based test). This is the preferable situation because the Abbott test can be used at high viral loads without the trapping device and at low viral loads with the trapping device. If the number of particles captured is less than 30 but greater than 5, it can still be quantified using other tests (e.g., a quantitative PCR based test available from LabCorp). The tables below show the great deal of variation possible in binding efficiency while still having a sufficiently sensitive device for both the SVC and the hepatic veins.

TABLE 1

| Viral Particles Captured - SVC | | | |
|---|---|---|---|
| Binding Efficiency | 10 Viral Particles/mL | 5 Viral Particles/mL | 1 Viral Particles/mL |
| 10% | 85050 | 42525 | 8505 |
| 5% | 42525 | 21263 | 4253 |
| 1% | 8505 | 4253 | 851 |
| 0.10% | 851 | 425 | 85 |
| 0.01% | 85 | 43 | 9 |

TABLE 2

| Viral Particles Captured - Hepatic Veins | | | |
|---|---|---|---|
| Binding Efficiency | 10 Viral Particles/mL | 5 Viral Particles/mL | 1 Viral Particles/mL |
| 10% | 21294 | 10647 | 2129 |
| 5% | 10647 | 5324 | 1065 |
| 1% | 2129 | 1065 | 213 |
| 0.10% | 213 | 106 | 21 |
| 0.01% | 21 | 11 | 2 |

Tables 1 and 2 illustrate that, when placed in a hepatic vein or SVC, the device may be able to capture a suitable number of viral particles for detection even if the concentration is 5 to 30 times less than what can be detected with one of the most commonly used tests. For example, for a traditional test that requires the presence of 30 viral particles, detection can be achieved at a binding efficiency as low as 0.1% in the SVC. If the device is placed in the hepatic veins, it would still be effective at a binding efficiency of 1% if the concentration in the blood were 1 viral particle per mL. In applications where the virus replicates in the liver (e.g. hepatitis C), it may be desirable to place the device in the hepatic veins as there may be a greater viral concentration than present in the SVC. The number of viral particles captured, as shown in Table 2, does not assume any increased concentration by placing the device closer to the liver. If the device is placed in the hepatic veins, it would be expected that the number of hepatitis C viral particles captured would be much greater than what is shown in Table 2. Furthermore, these calculations assume that the part of the device that crosses the vein is the only part of the device that is able to trap viral particles. It is clear from the above tables that the device is effective at low binding efficiencies.

In some embodiments, shapes other than the twisted coil may be used. For example, although not preferred for the application of hepatitis C, a straight rod design may also be used. This straight rod may be coated with antibodies on its exterior cylindrical surface and passed through a catheter for deployment into either the superior vena cava or hepatic veins. The relatively low sampling capabilities of this approach, compared to the twisted coil, are attributed to the strong reliance on having particles diffuse to the surface of the device before binding could occur.

Figure 2:
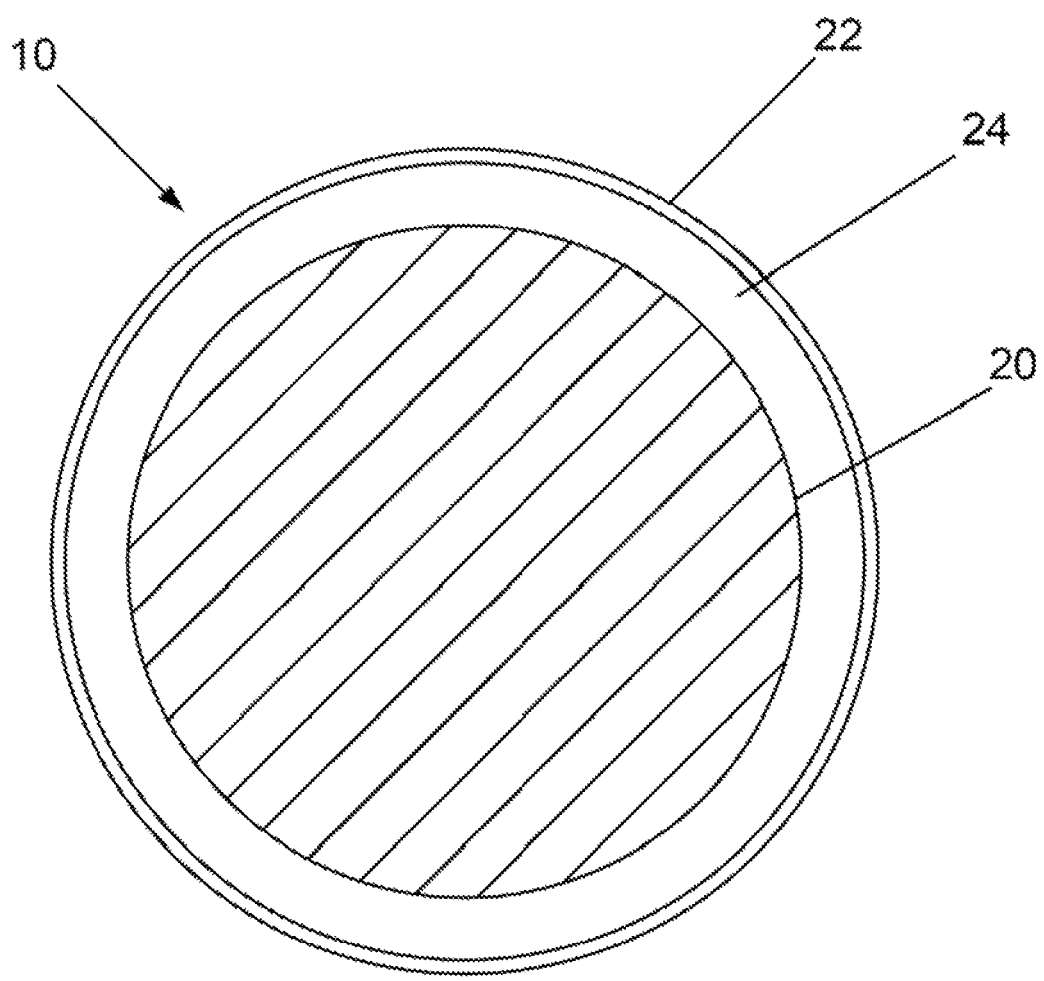
FIG. 2 is a section view, illustrating a viral particle trapping device according to one or more embodiments of the present invention.

In an exemplary embodiment, as illustrated in FIG. 2, the device 10 may include a structural substrate 20, one or more binding agents 22, and a coating 24 to enhance the attachment of the binding agents 22 to the structural substrate 20. The structural substrate 20 may be made of various materials, including metals and polymers. The structural substrate may also be elastic. In one embodiment, the structural substrate 20 is formed of NITINOL (NiTi). NITINOL is highly elastic, compared to other metals, and may be formed in such a way as to allow the device to be deformed for deployment to a sampling site through a catheter. The structural substrate 20 may then regain its original pre-deformed shape once deployed in the blood vessel. In this way, the device may, under the load of the catheter wall, assume a relatively low-profile configuration for ease of deployment through the catheter and then, once released from the catheter, spontaneously assume a relatively high-profile configuration at the viral trapping deployment site. Following the specified period of viral trapping, the device may be pulled back into the catheter in the relatively low-profile configuration.

A structural substrate 20 comprising NITINOL may be manufactured by a multistep process. For example, a NITI- NOL wire may be set in a fixture or on a mandrel that is in the shape of the desired device, and then heat treated. The heat treatment process can be achieved, for example, by using an air or vacuum furnace, salt bath, sand bath, heated die or other heating method. The temperature may be raised to a range of 500° C. to 550° C. during the heat treatment process. The treatment duration may be long enough for the entire material to reach the desired temperature. The heat treated NITINOL may then be quenched in a water bath. Finally, the NITINOL wire may be electropolished.

The coating 24 may be any material suitable for binding or attaching the antibodies 22 to the structural substrate 20. In some embodiments, the coating 24 comprises a polymeric material. In certain embodiments, the polymer is PDMS (polydimethylsiloxane). The PDMS may be mixed with a curing agent, such as Sylgard 184 (Dow Corning), and then degassed. The NITINOL wire may be dipped in this mixture and then removed and allowed to cure. Alternatively, other coating processes known in the art may be used. PDMS may bind to Ti alloys through a Si—O—Ti bond. The coated wire may then be placed in a plasma cleaner (e.g., PDC-32F, Harrick Scientific) after the curing process is completed. The plasma cleaning process may sterilize the surface and prepare the surface for bonding.

The binding agents 22 may be any antibodies suitable for trapping the viral particles of interest. For example, the binding agents 22 may be humanized and non-humanized antibodies. In HCV applications, the antibodies may be specific to the E1 or E2 antigens present on the envelope of the HCV viral particle. Using a humanized antibody decreases immune response if the antibodies become dislodged from the device while it is in the body. It is, however, possible that a non-humanized version would work because the device is only in the body for 30 minutes.

In one embodiment, the surface of the PDMS may be treated with a 2% solution of 3-mercaptoproyltrimethosilane in toluene for a one hour period to promote the binding of the antibodies to the polymer. The surface may then be dried and treated with 2 mM GBMS (N-γ-maleimidobutyryloxy succinimide ester) for one hour and then rinsed with PBS (phosphate buffered saline). A solution of antibodies may then be introduced to the chemically treated PDMS for 30 minutes at room temperature to react with the GBMS.

The specifics of the packaging and storage may be dictated by the antibody choice. The NITINOL and the PDMS are able to be stored at room temperature without altering their functions. However, some antibodies must be kept at −20° C. to avoid damage. Some antibodies must also not be thawed and refrozen, because doing so may damage their function.

Once the device has been manufactured, it may be packaged for transport and storage until it is needed for a diagnostic procedure. In one embodiment, the device is packaged in a rigid or flexible pouch, which may be composed for example of metal foil and/or polymer films. The packaged device may be sterilized, for example, by gamma irradiation or other techniques known in the art. The device preferably remains sterilized until deployment in the patient's body.

In one embodiment, a sterilized kit is provided which includes one or more viral particle trapping devices described herein and a deployment catheter sized for passage of the viral trapping device through the lumen of the catheter. The kit may comprise a viral particle trapping device and deployment catheter packaged together, for example within a single pouch. The kit may further include a stylet and/or grasping instrument for deployment and/or retrieval of the viral trap particle trapping device.

Methods

In another aspect of the present disclosure, a method is provided for measuring the concentration of viral particles of a fluid. The method may include deploying a viral particle trapping device in a blood vessel, and thereafter removing the device to determine the viral particle concentration of the fluid being sampled or alternatively to detect the presence of viral particles in the fluid.

The device may be deployed in various blood vessels. The preferred location of deployment may depend on the ease of deployment, the size of the vessel and the proximity of the blood vessel to areas of the patient's body with the highest viral loads, i.e., regions where the viral particles are expected to be in higher concentrations and the targeted medical analyte. The ease of deployment refers to how easy it is to deploy and remove the device. The size of the vessel is important because the amount of blood that can be sampled is related to the size of the vessel. The proximity of the deployment site to high viral loads may depend on the type of viral particles that are to be trapped. In HCV applications, proximity to the liver is relevant because the liver is the site of replication for the hepatitis C virus.

One preferred location for deployment in HCV applications is the hepatic veins. The hepatic veins carry blood from the liver to the inferior vena cava. It has been shown that the liver tissue has a 40 times higher concentration of viral RNA than peripheral blood. For deployment of the HCV trapping device in the hepatic veins, the device may be delivered via the coronary vein or femoral vein. A flexible polymeric catheter may be passed into either the leg or neck, depending on deployment location. An x-ray dye may be injected into the catheter and images of the vein may be taken. The physician may then pass the viral particle trapping device through the catheter to the deployment site. The catheter may be left in place during sampling. For example, the viral trapping device may remain deployed for about 30 minutes. The device then may be retrieved through the catheter after the sampling has ended, and the catheter then may be removed from the body.

Another preferred location for deployment when capturing hepatitis C viral particles is the superior vena cava (SVC). The SVC carries de-oxygenated blood from the upper half of the body to the right atrium. The SVC has a larger diameter (3-4 cm) than the hepatic veins (1.5 cm) to place the device and a blood velocity (avg. blood velocity=22.5 cm/s) that will allow for sufficient blood sampling capabilities. Although this location is further from the liver, the device would be exposed to more total blood flow over the same amount of time. For SVC deployment, the procedure is much simpler. Placement in the SVC may be performed using a peripherally inserted central catheter (PICC) line.

In one embodiment of the disclosed devices and methods for hepatitis C detection, a sample may be prepared for analysis by removing the viral particle trapping device from the body and placing it in blood collected from the patient. For example, the device may be placed in 2 mL of the patient's blood. The blood and trapping device, with bound viral particles, may then be incubated. Incubation would release the RNA contained in the viral particles. Incubation may be performed in a buffer solution to protect the RNA from RNAases. The structural substrate of the viral particle trapping device then may be removed from the blood sample and the sample may be processed using the same processes that are used to quantify a viral load in traditional blood draw. This method of sample preparation and analysis may also be used for detection of other viral particles besides hepatitis C.

The viral content of the blood sample may be quantified using any test suitable for detecting the presence of the viral particle or quantifying the amount of the viral particle present. For example, the blood sample may be analyzed using Real Time-Polymerase Chain Reaction (RT-PCR) based tests. For HCV applications, the blood sample may be analyzed using the COBAS™ AmpliPrep/COBAS™ TAQ-MAN™ HCV test, an in vitro nucleic acid amplification test, manufactured by Roche or the Abbott test discussed previously. This test measures viral load by quantifying the amount of RNA present in a fixed sample of blood.

The detection or quantification of viral particles may also be done using ELISA, fluorescence analysis, or mass spectroscopy. This may be done independent of the quantification using PCR or TMA.

In another embodiment, the viral particle trapping device described herein may be used in an in vitro diagnostic system, for example, by contacting a withdrawn sample of a biological fluid with the device. In one example, a fluid sample may be pumped through a channel or tube (e.g. during dialysis) in which the viral particle trapping device is located.

The device may also be used in veterinary and other non-human applications. For example, it is often important to closely monitor the concentration of viral particles or other medical analytes during the animal testing stage of development for medical devices and pharmaceuticals. The device could be deployed and retrieved from a non-human mammal in a similar manner to the human application. Alternatively, the device could also be placed in the animal and then removed after the animal is sacrificed.

The device may also be used to trap other medical analytes such as hepatitis A viral particles, hepatitis B viral particles, HIV (human immunodeficiency virus) viral particles, HPV (human papillomavirus) viral particles, circulating cancer cells, or circulating DNA. Additionally, the device may be used to trap pathogens or bacteria. The placement location of the device may be dictated by the analyte being targeted but may include, for example, bloods vessels, the bladders or the subarachnoid space in human other mammalian subjects or patients.

The trapping device may also be used for removing unwanted particles, molecules, objects or other medical analytes from the blood. The device would be deployed in the same manner as when used to trap HCV particles for quantification or detection. The duration of deployment in the body would be dictated by the amount of the targeted particle, molecule or object that is desired to be removed. The location of deployment may also be dictated by the desired target and the desired length of deployment. The device would selectively sample the blood and remove unwanted constituent without the blood being removed from the body. This may also remove target constituents or medical analytes from other bodily fluid.

The present description may be further understood with reference to the following non-limiting examples.

Example 1

Production of Trapping Devices

Trapping devices were prepared as follows.
Wire Preparation
A superelastic NITINOL (NiTi) wire 0.009 inches thick was used to form the core, or structural substrate, of the trapping device. Two geometries of devices were constructed: straight wires and coiled wires. To form the coiled wires, the NiTi wire was wound around a spiral mold with a diameter of 9 mm, a pitch of 3 mm and a length of 120 mm. and placed in an oven at 500° C. for 10 minutes. The coil was then quenched in water at room temperature. The resulting wire was set in a spiral shape but remained superelastic due to the quenching step.

PDMS Coating
The NiTi wire was subsequently coated with PDMS using the following steps in order to attach the biomolecules necessary for target detection:
1. The NiTi wires were cut to the desired length and held by each end with conductive alligator clips.
2. A beaker was filled with 35 g polydimethyl siloxane (PDMS) (Sylgard 184® at a ratio of 10:1 prepolymer: curing agent) and degassed under vacuum until no bubbles were visible (average time of 1 hour).
3. The wire was introduced in the PDMS bath and the alligator clips were connected to a DC power source and a switch to control the flow of current.
4. A current of 1.5 A was passed through the wire for 18 seconds, heating the wire such that a layer of liquid PDMS surrounding it was partially cured and attached to the wire.
5. The wire was rinsed in a bath of toluene so that any uncured PDMS was removed.
6. The coated wire was then cured at 80° C. for 1 hour.

The average thickness coating of each wire was 100 microns, or 0.1 mm for the conditions described above. For the experiment described in Example 2 below, the NiTi wire length was 30 mm, with a PDMS-coated region of about 25 mm.

Chemical Activation of Wires
The wire was exposed to air plasma once the PDMS had cured on the NiTi core. This process activated the PDMS surface, resulting in surface hydroxyl groups (—OH). These hydroxyl groups facilitate the attachment of polymers and biomolecules. Uniform activation of the surface was achieved by use of a custom apparatus, as follows:

Two DC motors (12V, 2 A and a maximum speed of 50 rpm) were deployed so as to make the wire rotate and move vertically. An electronic controller (arduino one motherboard) coordinated the motors so the movement of the wire was controlled.

The PDMS coated wire was attached on one end to the motor that gives the rotary movement and on the other to a 500-g iron counterweight. The counterweight ensured that the wire was straight, improving the uniformity of activation.

Two corona discharge coils were placed on opposite sides of the diameter of the wire, each 4 mm from the PDMS surface.

The process of activation was optimized so that the entire length of an 8-cm wire was drawn twice past the plasma coils every 40 seconds. The system performed twelve passes (a total activation time of 480 seconds) to assure that the activation was complete and uniform. The PDMS surface was observed to be hydrophilic after treatment with a water contact angle of lower than 20°.

Chemical Treatment of Wires
The activated PDMS coated wires were then treated to attach affinity ligands required to capture the target analyte. This process involved two stages: first, modify the surface to prevent nonspecific binding to PDMS; and second, attach the affinity ligand to the surface. The affinity ligand for this example was biotin and the model analyte was streptavidin but this strategy can be used with other affinity/analyte system. The wires were treated in four steps.
1. The activated PMDS surface was treated with polyethylene glycol (PEG) silane to prevent nonspecific binding of protein to the surface. The wire was immersed in a 0.05 molar solution of PEG-silane in toluene for 30 minutes to an hour. After this step, PEG is covalently bound to the surface of the PDMS. Covalent binding of PEG to PDMS was confirmed using contact angle measurements. After activation, PDMS is hydrophilic but reverts to its natural hydrophobic nature in 12-24 hours (100-110°). The contact angle of PEG-treated samples was tracked over several weeks. Before each measurement, the samples were rinsed with deionized water at moderate pressure and dried with nitrogen, ensuring that any dirt or noncovalently bound PEG was removed. The contact angle for PEG-treated PDMS was repeatable, stable and significantly lower than that of bare PDMS: contact angles ranging from 20 to 60° (depending on the PEG treatment time) were measured.

2. 3-aminopropyl triethoxysilane (APTES) was added to the solution of PEG-silane so that the complete solution was 10% APTES by volume. APTES is the first step in the chemical scaffold that attaches the affinity protein to the surface. It reacted with the —OH groups on activated PDMS, leaving primary amine groups on the surface, and the wire was removed from the solution after 30 minutes and rinsed with toluene.

APTES binding to PDMS after treatment with PEG-silane was confirmed using a fluorescamine assay. Fluorescamine is a molecule that forms fluorescent products upon reaction with a primary amine group, though fluorescamine itself is non-fluorescent. Flat pieces of activated PDMS were treated with 0.01M solution of PEG-silane in toluene for 30 minutes and 60 minutes before adding APTES to make the final solution 10% APTES by volume. Other samples were treated with the same solution but with both PEG-silane and APTES present from the start. The PDMS was treated with APTES for 30 minutes, removed and allowed to dry before being cut and placed in a 96-well plate. 50 uL of 3 mg/mL fluorescamine in dimethyl sulfoxide (DMSO) were pipetted into each well and a plate reader was used to examine the samples' fluorescence. The fluorescence intensity across all samples was within a factor of 2, and all samples had intensity over an order of magnitude higher than blank wells (filled only with fluorescamine solution and buffer).

3. The wires were submerged in a solution of 0.5 mg/mL NHS-LC-Biotin in dry DMSO for two hours. This step attached the affinity protein to the PDMS surface.

4. The wires were then rinsed with DMSO and stored in phosphate-buffered saline (PBS) prior to use in the binding experiment described in Example 2 below.

Example 2

Binding Experiment Using Trapping Device

Four treated wires were used: two only with PEG-silane, and two with the complete sequence of chemical treatment described in Example 1 above. The PEG-only wires were used as control samples for the wires that were fully treated. All wires were placed individually in vials with a solution of streptavidin-coated fluorescent beads, 6 microns in diameter. Each 5-mL vial contained approximately 20000 beads. The vials were placed in an orbital shaker for 24 hours ensuring longitudinal flow over the wire.

Results

Confocal fluorescence microscopy was used to image the wires after submersion in the particle solution. Particles were only observed close to where the PMDS coating ended and the NiTi wire was exposed. The results are listed in Table 3 below.

Figure 3:
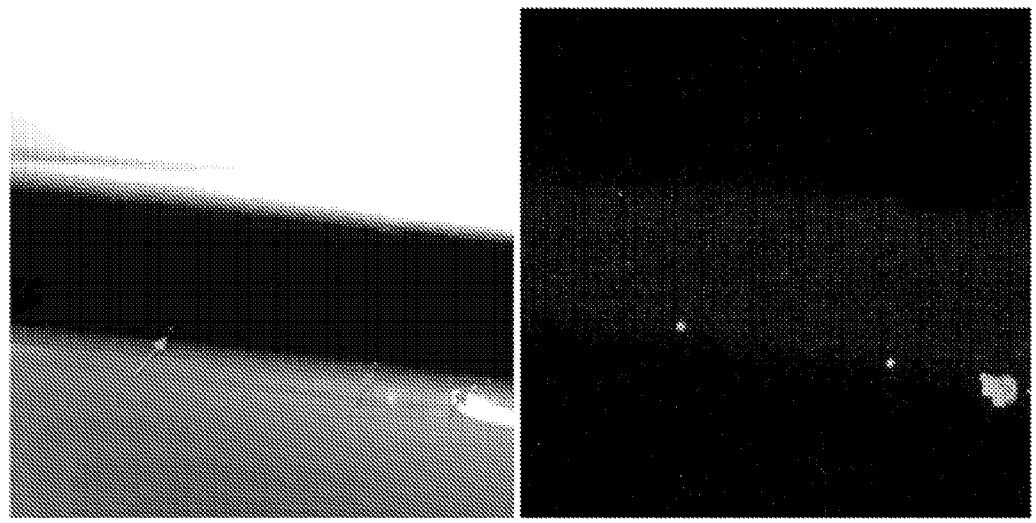
FIG. 3 shows images of a trapping device, made according to an embodiment of the present invention, which has trapped streptavidin-coated fluorescent beads.

FIG. 3 shows one end of a biotin-coated device with bound particles. The image on the left is a light image of device with particles highlighted by red arrows, and the image on the right is a fluorescence image of the same region of the device. Bead identification was confirmed by fluorescence. It is noted that the cluster of beads at the far right of both images (FIG. 3) was not counted towards the number of beads bound to the wire. These microparticle aggregates form in the stock solution of particles and are usually removed by repeated washing of the microbeads before diluting them for a binding experiment.

TABLE 3

|  | Biotin wire 1 | Biotin wire 2 | Control wire 1 | Control wire 2 |
|---|---|---|---|---|
| Number of particles found (total) | 4 | 5 | 1 | 0 |

It will be appreciated that various embodiments of the above disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

We claim:

1. A trapping device for capturing a medical analyte, comprising:
    a structural substrate which has a twisted coil configuration; and
    at least one binding agent affixed as part of a coating on the structural substrate, the binding agent being capable of binding or attaching with the medical analyte,
    wherein the trapping device is dimensioned and adapted for placement in a blood vessel in a patient, the trapping device being configured to trap at least a portion of the medical analyte present in blood flowing through the blood vessel, and
    wherein, following said placement, the twisted coil comprises loops that cross back and forth across a lumen of the blood vessel.

2. The trapping device of claim 1, wherein the binding agent is an antibody or aptamer.

3. The trapping device of claim 1, wherein the medical analyte is a viral particle, cell, or circulating DNA.

4. The trapping device of claim 1, wherein the structural substrate comprises a nickel titanium alloy.

5. The trapping device of claim 1, wherein the binding agent is affixed to a surface of the trapping device.

6. The trapping device of claim 5, wherein the binding agent comprises a plurality of antibodies affixed to at least a portion of the surface of the trapping device.

7. The trapping device of claim 6, wherein the antibodies are affixed to the structural substrate by a polymeric material.

8. The trapping device of claim 7, wherein the polymeric material comprises polydimethylsiloxane.

9. The trapping device of claim 6, wherein the antibodies are capable of binding to Hepatitis C Virus (HCV) viral particles.

10. The trapping device of claim 9, wherein the antibodies bind to E1 or E2 antigens present on the HCV viral particles.

11. A viral particle trapping device for sampling a viral particle, comprising:
- a structural substrate in a twisted coil configuration;
- a polymeric coating on the structural substrate; and
- a plurality of antibodies capable of binding with the viral particle, the antibodies being affixed to the polymeric coating on the structural substrate;
- wherein the trapping device is dimensioned and adapted for placement in a blood vessel in a patient, the trapping device being configured to trap one or more viral particles present in blood flowing through the blood vessel, and
- wherein, following said placement, the twisted coil comprises loops that cross back and forth across a lumen of the blood vessel.

12. The viral particle trapping device of claim 11, wherein the structural substrate comprises a nickel titanium alloy wire.

* * * * *